United States Patent
Belanoff

(10) Patent No.: US 11,103,514 B2
(45) Date of Patent: Aug. 31, 2021

(54) TREATMENT OF MUSCULAR DYSTROPHY

(75) Inventor: Joseph Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 13/116,239

(22) Filed: May 26, 2011

(65) Prior Publication Data

US 2011/0294771 A1 Dec. 1, 2011

Related U.S. Application Data

(60) Provisional application No. 61/348,553, filed on May 26, 2010.

(51) Int. Cl.
*A61K 31/567* (2006.01)
*A61K 31/569* (2006.01)

(52) U.S. Cl.
CPC .......... *A61K 31/567* (2013.01); *A61K 31/569* (2013.01)

(58) Field of Classification Search
CPC .. A61K 31/567; A61K 31/569; A61K 31/575; A61P 21/04; A61P 21/00
USPC ........................................................ 514/179
See application file for complete search history.

(56) References Cited

U.S. PATENT DOCUMENTS

| | | | | |
|---|---|---|---|---|
| 5,380,839 A | | 1/1995 | McCall et al. | |
| 6,150,349 A | * | 11/2000 | Schatzberg | A61K 31/00 514/179 |
| 6,303,591 B1 | * | 10/2001 | Burton et al. | 514/179 |
| 6,369,046 B1 | * | 4/2002 | Schatzberg | A61K 31/00 514/167 |
| 6,875,418 B2 | * | 4/2005 | Hampton | A61K 49/0004 424/9.1 |
| 6,964,953 B2 | * | 11/2005 | Belanoff | A61K 31/56 514/178 |
| 7,402,578 B2 | * | 7/2008 | Belanoff | A61K 31/56 424/145.1 |
| 7,888,486 B2 | * | 2/2011 | Walsh | C07K 16/22 530/388.24 |
| 7,910,107 B2 | * | 3/2011 | Walsh | C07K 16/22 424/145.1 |
| 8,598,149 B2 | * | 12/2013 | Belanoff | A61K 31/56 514/178 |
| 8,703,752 B2 | * | 4/2014 | Ruat | A61K 31/56 514/114 |
| 8,895,309 B2 | * | 11/2014 | Kaspar | A61K 38/18 435/456 |
| 8,921,348 B2 | * | 12/2014 | Belanoff | A61K 31/56 514/178 |
| 2002/0169152 A1 | * | 11/2002 | Belanoff | A61K 31/56 514/179 |
| 2003/0061974 A1 | | 4/2003 | Belanoff | |
| 2003/0064947 A1 | * | 4/2003 | Belanoff | A61K 31/56 514/179 |
| 2003/0064974 A1 | * | 4/2003 | Belanoff | A61K 31/56 514/179 |
| 2005/0085464 A1 | * | 4/2005 | Sapse | A61K 31/70 514/220 |
| 2007/0087000 A1 | * | 4/2007 | Walsh | C07K 16/22 424/145.1 |
| 2007/0259837 A1 | * | 11/2007 | Meier | A61K 31/355 514/152 |

FOREIGN PATENT DOCUMENTS

WO 98/26783 6/1998
WO 2010/002901 A1 1/2010

OTHER PUBLICATIONS

Konagaya et al..(Endocrinology. Jul. 1986; 119(1):375-80).*
Use of mifepristone to antagonize endogenous cortisol might also be of benefit in a wide variety of disorders. Spitz and Bardin (in press) reviewed some of these potential uses such as attenuation of muscle atrophy associated with androgen withdrawal, denervation, and muscular dystrophy.*
Raaijmakers et al. (The Journal of Bio;ogical Chemistry vol. 284, No. 29, p. 19579, Jul. 17, 2009).*
Sasha Bogdanovich et al. (The Faseb Journal-Research communication, 19, 543-549 (2005), Myosatatin propeptide-mediated amelioration of dystrophic pathophysiology).*
Kun Ma et al. (Am J Physiol Endocrineol Metab 285:E363-E371,2003, First published Apr. 29, 2003).*
C A Beck et al. (Endocrinology, vol. 133, Issue 2, Aug. 1, 1993, pp. 728-740, abstract).*
Pillers et al. (Investigative Ophthalmology and Visual Science May 2007, vol. 48, 3772), Arvo Annual Meeting abstract, pp. 1-2).*
Ma et al., "Glucocortoid-Induced Skeletal Muscle Atrophy is Associated with Upregulation of Myostatin Gene Expression," *Am. J. Physiol. Endocrinol Metab.*, 285; E363-E371 (2003).
Song et al., "Muscle-Specific Expression of IGF-1 Blocks Angiotensin II-Induced Skeletal Muscke Wasting," The Journal of Clinical Investigation, vol. 115, No. 2, Feb. 2005, 451-458.
Mohler et al., "Non-Steroidal Glucocorticoid Receptor Antagonists: The Race to Replace RU-486 for Anti-Glucocorticoid Therapy," Expert Opinions on Therapeutic Patents, Informa Healthcare, GB, vol. 17, No. 1, Jan. 1, 2007, pp. 59-81.
Manzur et al., "Glucocorticoid Corticosteroids for Duchenne Muscular Dystrophy," The Cochrane Library, Cochrane Database Syst. Rev., vol. 2009, No. 3, Jan. 2009, pp. 1-72.
Rüegg et al., "Molecular Mechanisms and Treatment Options for Muscle Wasting Diseases," Annual review of Pharmacology and Toxicology, vol. 51, No. 1, Feb. 10, 2011, pp. 373-395.
De Luca, "Pre-clinical drug tests in the mdx mouse as a model of dystrophinopathies: an overview," *Acta Myologies* 2012, XXXI: p. 40-47.
Morris et al., "Bowman-Birk inhibitor attenuates dystrophic pathology in mdx mice," *J. Appl. Physiol.*, 2010, 109:1492-1499.

* cited by examiner

*Primary Examiner* — Sabiha N Qazi
(74) *Attorney, Agent, or Firm* — Kilpatrick Townsend & Stockton LLP

(57) ABSTRACT

The present invention resides in the discovery that glucocorticoid receptor antagonists are effective for treating muscular dystrophy including type 1 or type 2 myotonic dystrophy. Treatment methods and kits are provided.

12 Claims, No Drawings

TREATMENT OF MUSCULAR DYSTROPHY

RELATED APPLICATIONS

This application claims priority to U.S. Patent Application Ser. No. 61/348,553, filed May 26, 2010, the contents of which are hereby incorporated by reference in the entirety.

BACKGROUND OF THE INVENTION

Muscular dystrophies are a group of more than 30 genetic diseases characterized by progressive weakness and degeneration of the skeletal muscles that control movement. Some forms of muscular dystrophy are seen in infancy or childhood, while others may not appear until middle age or later. The disorders differ in terms of the distribution and extent of muscle weakness, age of onset, rate of progression, and pattern of inheritance. The various types of muscular dystrophy affect more than 50,000 Americans.

Duchenne muscular dystrophy (DMD) is the most common form of muscular dystrophy with an occurrence rate of about one in 3,500 males worldwide. In DMD, very little of the protein dystrophin is produced. This protein is essential for muscle integrity. Onset of the disease is between 3 and 5 years and the disorder progresses rapidly. Most boys are unable to walk by age 12, and later need a respirator to breathe. Myotonic dystrophy is the second most common form of muscular dystrophy after DMD with a worldwide occurrence of about one in 20,000, and is the most common form of muscular dystrophy affecting adults. Two types of adult onset myotonic dystrophy exist. Type 1 (DM1), also known as Steinert's Disease, represents about 98% of all myotonic dystrophy cases. The rarer Type 2 disease, DM2, is also known as proximal myotonic myopathy (PROMM).

DM1 is an autosomal-dominant disease caused by expansion of cytosine-thymine-guanine (CTG) trinucleotide repeats in exon 15 of the myotonic dystrophy protein kinase (DMPK) gene found on chromosome 19q13.3. The protein encoded by this gene is a serine-threonine kinase that is closely related to other kinases that interact with members of the Rho family of small GTPases. Substrates for this enzyme include myogenin, the beta-subunit of the L-type calcium channels, and phospholemman. The 3' untranslated region of this gene normally contains 5-34 copies of a CTG trinucleotide repeat. Increased copy number of the CTG repeat results in DM1 with disease severity increasing with increased repeat copy number. About 50 or more CTG repeats cause mild to classical adult-onset myotonic dystrophy and 700 to greater than 3000 repeats often result in the severe congenital form of the disease.

DM2 is due to a CCTG repeat in intron 1 of the CNBP (also known as ZNF9) gene on chromosome 3q21.3. This gene codes for a CCHC-type zinc finger, nucleic acid binding protein, the function of which remains unclear. The repeat expansion for DM2 is much larger than for DM1, ranging from 75 to over 11,000 repeats. Unlike in DM1, the size of the repeated DNA expansion in DM2 does not appear to make a difference in the age of onset or disease severity.

Because of the debilitating and progressive nature of muscular dystrophies, including mytonic muscular dystrophy, the resulting disability and loss of quality of life in patients, the significant cost of supportive care, and the lack of ultimate cure, there exists an urgent need for new and effective means to halt progression and ameliorate suffering of afflicted individuals. The present invention fulfills this and other related needs.

BRIEF SUMMARY OF THE INVENTION

In one aspect, this invention provides a method for treating a patient suffering from a muscular dystrophy. The method comprises administering to the patient an effective amount of a glucocorticoid receptor antagonist to ameliorate the symptoms of muscular dystrophy, provided that the patient is not otherwise in need of treatment with a glucocorticoid receptor antagonist.

In some embodiments, the patient suffers from a muscular dystrophy and is administered a composition consisting essentially of a glucocorticoid receptor antagonist in an amount effective to ameliorate the symptoms of the condition.

In other embodiments, the patient suffers from a specific type of muscular dystrophy, such as myotonic dystrophy (e.g., type 1 myotonic dystrophy or type 2 myotonic dystrophy), and is administered an effective amount of a glucocorticoid receptor antagonist to ameliorate the symptoms of the condition. In some cases, the composition administered to the patient comprises a glucocorticoid receptor antagonist in an amount effective to ameliorate the symptoms of the condition. In other cases, the composition administered to the patient consists essentially of a glucocorticoid receptor antagonist in an amount effective to ameliorate the symptoms of the condition.

In some embodiments, the glucocorticoid receptor antagonist used in the method of this invention comprises a steroidal skeleton with at least one phenyl-containing moiety in the 11-β position of the steroidal skeleton. For example, the phenyl-containing moiety in the 11-β position of the steroidal skeleton is a dimethylaminophenyl moiety.

Some exemplary glucocorticoid receptor antagonists include mifepristone, 11β-(4-dimethylaminoethoxyphenyl)-17α-propynyl-17β-hydroxy-4,9 estradien-3-one, 17β-hydroxy-17α-19-(4-methylphenyl)androsta-4,9(11)-dien-3-one, 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol, and (11β,17β)-11-(1,3-benzodioxo-5-yl)-17-hydroxy-17-(1-propynyl)estra-4,9-dien-3-one. They may be administered according to different schedules, such as once per day. In some case they may be administered orally; or they may be administered by transdermal application, by a nebulized suspension, or by an aerosol spray.

In a second aspect, the present invention provides a kit for ameliorating the symptoms of muscular dystrophy in a patient, who is not otherwise in need of treatment of a condition by the use of a glucocorticoid receptor antagonist. The kit comprising: (i) a glucocorticoid receptor antagonist; and, (ii) an instructional material providing the indications, dosage, and schedule of administration of the glucocorticoid receptor antagonist to a patient suffering from muscular dystrophy. In some embodiments, the glucocorticoid receptor antagonist is mifepristone, which may be in the tablet form for patient administration. In other embodiments, the kit is used for treating a particular type of muscular dystrophy, such as myotonic dystrophy (e.g., type 1 myotonic dystrophy or type 2 myotonic dystrophy).

DEFINITIONS

The term "muscular dystrophy," as used herein, refers to any hereditary condition or disorder that affect skeletal muscle and is characterized by progressive muscle weakness, defects in muscle proteins, and ultimately muscle cell death. This term broadly encompasses any condition that involves at least one and typically more symptoms including muscle pain, muscle weakness, muscle stiffness, difficulty in walking, myotonia, fatigue, scoliosis, axonal peripheral neuropathy, cardiomyopathy, cardiac arrhythmia, mental retardation, hypersomnia, sleep apnea, iridescent posterior subcapsular cataracts, insulin insensitivity, type II diabetes mellitus, premature balding, testicular failure, infantile hypotonia, and respiratory deficits. Not all symptoms need to be present. For example, a person with muscular dystrophy may exhibit cataracts or mild myotonia, but not muscular weakness or cardiac arrhythmia. Similarly, a person with muscular dystrophy may exhibit muscular pain and weakness, but not hypersomnia or sleep apnea.

The terms "myotonic dystrophy type 1" or "DM1" is also known as Steinert's Disease, a condition where the patient has an abnormally large number of CTG repeats in the patient's DMPK gene. Typically, symptoms are noted in individuals with 50 or greater CTG repeats. DM1 includes patients with mild, classic and congenital forms (phenotypes) of the disease.

The terms "myotonic dystrophy type 2," "DM2," "proximal mytonic myopathy," and "PROMM" refer to a condition where the patient has an abnormally large number of CCTG repeats in their CNBP (ZNF9) gene. General symptoms are noted in individuals that have at least 75 CCTG repeats.

Typically, the number and severity of muscular dystrophy symptoms depends on the type and severity of the genetic defect. For example, with DM1, as the CTG copy number increases, the age at which symptoms manifest decreases with patients with higher copy numbers having more severe symptoms at a particular age compared to patients with a lower copy number. For milder forms of the disease, a patient may initially be asymptomatic and present with physical manifestations of the disease once adolescence or adulthood is reached.

The term "ameliorate," as used herein, refers to the effects of administering a glucocorticoid receptor antagonist to a muscular dystrophy patient (e.g., a myotonic dystrophy patent) that result in any indicia of success in the prevention, reduction, or reversal of one or more symptoms related to the condition. Reduction may be indicated in lesser severity, delayed onset of symptoms or a slowing of disease progression. The prevention, reduction, or reversal of symptoms can be measured based on objective parameters, such as the results of a physical examination or laboratory test (i.e., blood test), decreased need for medication (i.e., decrease in pain medication), decreased need for supportive measures (i.e., use of a ventilator), or increase in mobility. The prevention, reduction, or reversal of symptoms can be also measured based on subjective parameters, such as a reduction in pain or stiffness or increase in a patient's mobility and sense of wellbeing.

The term "effective amount," as used herein, refers to an amount of a substance that produces desired therapeutic effects resulting from the administration of the substance. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "cortisol" refers to a family of compounds also referred to as hydrocortisone, including any synthetic or natural analogues thereof.

The term "glucocorticoid receptor (GR)" refers to a family of intracellular receptors, also referred to as the cortisol receptor, that specifically bind to cortisol and/or cortisol analogs. The term includes isoforms of glucocorticoid receptor, recombinant glucocorticoid receptor, and mutated glucocorticoid receptor.

The term "mifepristone" refers to a family of compounds also referred to as RU486, or RU38.486, or 17-β-hydroxy-11-β-(4-dimethyl-aminophenyl)-17-α-(1-propynyl)-estra-4,9-dien-3-one), or 11-β-(4dimethylaminophenyl)-17-β-hydroxy-17-α-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11β-[p-(Dimethylamino)phenyl]-17β-hydroxy-17-(1-propynyl)-estra-4,9-dien-3-one; 11β-(4-dimethyl-aminophenyl)-17β-hydroxy-17α-(prop-1-ynyl)-estra-4,9-dien-3-one; 17β-hydroxy-11β-(4-dimethylamino- phenyl-1)-17α-(propynyl-1)-estra-4,9-diene-3-one; 17β-hydroxy-11β-(4-dimethylaminophenyl-1)-17α-(propynyl-1)-E; (11β,17β)-11-[4-dimethylamino)-phenyl]-17-hydroxy-17-(1-propynyl)estra-4,9-dien-3-one; and 11β-[4-(N,N-dimethylamino) phenyl]-17α-(prop-1-ynyl)-D-4,9-estradiene-17β-ol-3-one.

The term "glucocorticoid receptor antagonist (GRA)," as used herein, refers to any composition or compound that, by way of specifically binding to glucocorticoid receptor (GR), partially or completely inhibits or antagonizes the binding of a glucocorticoid receptor agonist, such as cortisol or a cortisol analog (synthetic or natural), to the glucocorticoid receptor. By "specific" or "specifically," it is intended that a GRA preferentially binds to the glucocorticoid receptor with an affinity higher than its binding affinity to the mineralocorticoid receptor (MR), typically at least 100-fold, and frequently at least 1000-fold higher.

A patient "not otherwise in need of treatment with a glucocorticoid receptor antagonist" is a patient who is not suffering from a condition known in the art to be effectively treatable with glucocorticoid receptor antagonists. Conditions known in the art to be effectively treatable with glucocorticoid receptor antagonists include Cushing's disease, drug withdrawal, psychosis, dementia, stress disorders, psychotic major depression, and weight gain induced by anti-psychotic medications.

A "composition consisting essentially of a glucocorticoid receptor antagonist" is a composition that contains only one therapeutically effective agent, the glucocorticoid receptor antagonist, but no other agents effective for the condition to be treated, such as muscular dystrophy or myotonic dystrophy. Such a composition may optionally contain one or more pharmaceutically or physiologically acceptable excipient.

DETAILED DESCRIPTION OF THE INVENTION

This invention pertains to the surprising discovery that agents capable of inhibiting glucocorticoid-induced biological responses via their ability to specifically bind glucocorticoid receptor are effective for treating or alleviating the symptoms of muscular dystrophy. In patients who have been diagnosed with the condition, the methods of the invention can preferably reverse or inhibit the worsening of symptoms related to such condition and/or prevent development of new symptoms. In one embodiment, the methods of the invention use agents that act as glucocorticoid receptor antagonists, to reverse or prevent symptoms of a muscular dystrophy, including type 1 or type 2 myotonic dystrophy. The methods of the invention are effective in treating a muscular dystrophy patient afflicted with either normal, increased or decreased levels of cortisol or other glucocorticoids, natural or synthetic.

Cortisol acts by binding to an intracellular glucocorticoid receptor (GR). In humans, glucocorticoid receptors are present in two forms: a ligand-binding glucocorticoid receptor-α of 777 amino acids; and, a glucocorticoid receptor-β isoform that differs in only the last fifteen amino acids. The two types of glucocorticoid receptor have high affinity for their specific ligands, and are considered to function through the same signal transduction pathways.

The biologic effects of cortisol, including pathologies or dysfunctions caused by hypercortisolemia, can be modulated and controlled at the glucocorticoid receptor level using receptor antagonists. Several different classes of agents are able to act as glucocorticoid receptor antagonists, i.e., to block the physiologic effects of glucocorticoid receptor-agonist binding (the natural agonist is cortisol). These antagonists include compositions, which, by binding to the glucocorticoid receptor, block the ability of an agonist to effectively bind to and/or activate the glucocorticoid receptor. One family of known glucocorticoid receptor antagonists, mifepristone and related compounds, are effective and potent anti-glucocorticoid agents in humans (Bertagna, *J. Clin. Endocrinol. Metab.* 59:25, 1984). Mifepristone binds to the glucocorticoid receptor with high affinity, with a K of dissociation $<10^{-9}$ M (Cadepond, *Annu. Rev. Med.* 48:129, 1997). Thus, in one embodiment of the invention, mifepristone and related compounds are used to treat muscular dystrophies.

Muscular dystrophy can be detected by regular physical examinations. Frequently as muscle weakness on manual motor testing of neck flexors and finger flexors, and later as symptomatic weakness often involving hip-girdle muscles in climbing stairs and arising from chairs. Myotonia can be identified by tapping a muscle with a reflex hammer or by observing repetitive spontaneous discharges on electromyography (EMG). Characteristic posterior subcapsular cataracts are visible on direct ophthalmoscopy or as pathognomonic posterior subcapsular red and green iridescent opacities on slit lamp examination. Muscular dystrophy-related cardiac conduction defects are detectable on routine electrocardiography (ECG). Approximately 75% of adults with DM1 or DM2 have hypogammaglobulinemia that can be detected by serum protein electrophoresis or immuno-protein electrophoresis. Insulin insensitivity and type II diabetes can be identified by a glucose tolerance test or blood glucose test. Primary gonadal failure in males can be detected by assaying for serum testosterone or FSH concentration. Confirmation of a muscular dystrophy diagnosis is by molecular genetic testing using standard techniques (i.e., PCR and Southern blotting). A variety of means are available for monitoring symptoms of the disease and for assessing the success of the treatment methods of the invention, i.e., the success and extent to which muscular dystrophy symptoms are reduced, reversed, or otherwise improved. These means typically involve the same physical examinations and standard medical laboratory testing procedures that are used in formulating the initial diagnosis.

I. Determination of a Muscular Dystrophy

Criteria for determining a muscular dystrophy condition are set forth above. A patient's muscle strength can be measured manually (i.e., Manual Muscle Testing or MMT), whereas respiratory muscle strength can be measured electronically by instruments such as pressure transducers, which are routinely used by health care practitioners in assessing respiratory health and capacity. The presence of cataracts can be ascertained through a physical examination.

Particular muscular dystrophy symptoms (e.g., hypothyrodism, insulin resistance, type II diabetes and low testosterone level) can be detected by standard laboratory tests. Standard laboratory equipment and well established testing protocols (e.g., glucose tolerance test) are available for assessing the relevant parameters, which are then compared with the established normal values or diagnostic standards, also well known to the medical practitioners, before a determination is made as to whether the patient has a muscular dystrophy condition. Confirmation of a suspected diagnosis, especially for a myotonic dystrophy, is by a molecular genetic test.

II. General Laboratory Procedures

When practicing the methods of the invention, a number of general laboratory tests can be used to assist in the progress of the patient under glucocorticoid receptor antagonist treatment, including monitoring of parameters such as blood cortisol, drug metabolism, etc. These procedures can be helpful because all patients metabolize and react to drugs uniquely. In addition, such monitoring may be important because each glucocorticoid receptor antagonist has different pharmacokinetics. Different patients and glucocorticoid receptor antagonists may require different dosage regimens and formulations. Such procedures and means to determine dosage regimens and formulations are well described in the scientific and patent literature. A few illustrative examples are set forth below.

A. Determining Blood Cortisol Levels

Varying levels of blood cortisol may be observed in patients suffering from a muscular dystrophy, although the present invention may also be practiced upon patients with apparently normal levels of blood cortisol. Thus, monitoring blood cortisol and determining baseline cortisol levels are useful laboratory tests to aid in treating muscular dystrophies. A wide variety of laboratory tests exist that can be used to determine whether an individual is normal, hypo- or hyper-cortisolemic. Patients who have developed muscular dystrophy symptoms may have normal levels of cortisol, which are often less than 25 μg/dl in the morning, and frequently about 15 μg/dl or less in the afternoon. The values often fall at the high end of the normal range, which is generally considered to be 5-15 μg/dl in the afternoon.

Immunoassays such as radioimmunoassays are commonly used for monitoring cortisol level because they are accurate, easy to do and relatively cheap. One such assay available in kit form is the radioimmunoassay available as "Double Antibody Cortisol Kit" (Diagnostic Products Corporation, Los Angeles, Calif.), (*Acta Psychiatr. Scand.* 70:239-247, 1984). This test is a competitive radioimmunoassay in which $^{125}$I-labeled cortisol competes with cortisol from a clinical sample for antibody sites. In this test, due to the specificity of the antibody and lack of any significant protein effect, serum and plasma samples require neither preextraction nor predilution.

B. Determining Blood and Urine GRA Levels

Because a patient's metabolism, clearance rate, toxicity levels, etc. differs with variations in underlying primary or secondary disease conditions, drug history, age, general medical condition and the like, it may be necessary to measure blood and urine levels of the glucocorticoid receptor antagonist used in the treatment method. Means for such monitoring are well described in the scientific and patent literature.

C. Other Laboratory Procedures

Because the mechanism of a muscular dystrophy including type 1 or type 2 myotonic dystrophy may be complex, a number of additional laboratory tests can be used adjunctively in the methods of the invention to assist in diagnosis, treatment efficacy, prognosis, toxicity and the like. For example, various testing may be conducted to assess a patient's muscle strength, flexibility, and range of motion. Other standard examination methods can be used to detect a patient's cardiac abnormality, reduced mental capacity, or male infertility. Also, diagnosis and treatment assessment can be augmented by monitoring and measuring glucocorticoid-sensitive variables, including but not limited to fasting blood sugar, blood sugar after oral glucose administration, plasma concentrations thyroid stimulating hormone (TSH), corticosteroid-binding globulin, luteinizing hormone (LH), testosterone-estradiol-binding globulin, leptin, insulin, and/or total and free testosterone.

Laboratory tests monitoring and measuring glucocorticoid receptor antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to mifepristone) can be determined using, for example, thin layer chromatography, as described in Kawai, *Pharmacol. and Experimental Therapeutics* 241:401-406, 1987.

III. Glucocoricoid Receptor Antagonists

The invention provides for methods of treating a muscular dystrophy utilizing any compound that can, via its specific binding to a glucocorticoid receptor, block a biological response associated with the binding of cortisol or a cortisol analogue to the glucocorticoid receptor. Specific antagonists of glucocorticoid receptor activity utilized in the methods of the invention are well described in the scientific and patent literature. A few illustrative examples are set forth below.

A. Steroidal Glucocorticoid Receptor Antagonists

Steroidal glucocorticoid receptor antagonists are administered to treat a muscular dystrophy in various embodiments of the invention. Steroidal glucocorticoid receptor antagonists can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid receptor antagonists include modifications of the 11-beta hydroxy group and modification of the 17-beta side chain (see, e.g., Lefebvre, *J. Steroid Biochem.* 33:557-563, 1989).

Examples of steroidal glucocorticoid receptor antagonists include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal glucocorticoid receptor antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and 17β-hydroxy-17α-19-(4-methylphenyl)androsta-4,9(11)-dien-3-one (RU044).

Other examples of steroidal antiglucocorticoids are disclosed in Van kampen et al. (2002) *Eur. J. Pharmacol.* 457(2-3):207, WO 03/043640, EP 0 683 172 B1, and EP 0 763 541 B1. Furthermore, EP 0 763 541 and Hoyberg et al., *Int'l J. Neuro-psychopharmacology*, Suppl. 1, S148 (2002) discloses the compound (11β,17β)-11-(1,3-benzodioxol-5-yl)-17-hydroxy-17-(1-propynyl)estra-4,9-dien-3-one (ORG 34517), which in some embodiments may be administered in an effective amount in the practice of the present invention.

1. Removal or Substitution of the 11-Beta Hydroxy Group

Glucocorticoid receptor agonists with modified steroidal backbones comprising removal or substitution of the 11-beta hydroxy group are administered in one embodiment of the invention. This class includes natural compounds, including cortexolone, progesterone and testosterone derivatives, and synthetic compounds, such as mifepristone (Lefebvre, et al. supra). Preferred embodiments of the invention include all 11-beta-aryl steroid backbone derivatives because these compounds are devoid of progesterone receptor (PR) binding activity (Agarwal, *FEBS* 217:221-226, 1987). Another preferred embodiment comprises an 11-beta phenyl-aminodimethyl steroid backbone derivative, i.e., mifepristone, which is both an effective glucocorticoid receptor antagonist and anti-progesterone agent. These compounds act as reversibly-binding steroid receptor antagonists. For example, when bound to a 11-beta phenyl-aminodimethyl steroid, the steroid receptor is maintained in a conformation that cannot bind its natural ligand, such as cortisol in the case of glucocorticoid receptor (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid receptors. Another 11-beta phenyl-aminodimethyl steroids shown to have glucocorticoid receptor antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, *J. Steroid Biochem. Molec. Biol.* 45:205-215, 1993). Another glucocorticoid receptor antagonist related to RU486 is RU044 (RU43.044) 17-beta-hydrox-17-alpha-19-(4-methyl-phenyl)-androsta-4,9 (11)-dien-3-one) (Bocquel, 1993, supra). See also Teutsch, *Steroids* 38:651-665, 1981; U.S. Pat. Nos. 4,386,085 and 4,912,097.

One embodiment includes compositions containing the basic glucocorticoid steroid structure, which are irreversible glucocorticoid receptor antagonists. Such compounds include alpha-keto-methanesulfonate derivatives of cortisol, including cortisol-21-mesylate(4-pregnene-11β, 17α,21-triol-3,20-dione-21-methane-sulfonate) and dexamethasone-21-mesylate (16-methyl-9 alpha-fluoro-1,4-pregnadiene-11 beta, 17-alpha, 21-triol-3, 20-dione-21-methane-sulfonate). See Simons, *J. Steroid Biochem.* 24:25-32, 1986; Mercier, *J. Steroid Biochem.* 25:11-20, 1986; and U.S. Pat. No. 4,296,206.

2. Modification of the 17-Beta Side Chain Group

Steroidal glucocorticoid receptor antagonists obtained by various structural modifications of the 17-beta side chain are also used in the methods of the invention. This class includes synthetic antiglucocorticoids such as dexamethasone-oxetanone, various 17,21-acetonide derivatives and 17-beta-carboxamide derivatives of dexamethasone (Lefebvre, 1989, supra; Rousseau, *Nature* 279:158-160, 1979).

3. Other Steroid Backbone Modifications glucocorticoid receptor antagonists used in the various embodiments of the invention include any steroid backbone modification that effects a biological response resulting from a glucocorticoid receptor-antagonist interaction. Steroid backbone antagonists can be any natural or synthetic variation of cortisol, such as adrenal steroids missing the C-19 methyl group, such as 19-nordeoxycorticosterone and 19-norprogesterone (Wynne, *Endocrinology* 107:1278-1280, 1980).

In general, the 11-beta side chain substituent, and particularly the size of that substituent, can play a key role in determining the extent of a steroid's glucocorticoid receptor antagonist activity. Substitutions in the A ring of the steroid backbone can also be important. 17-hydroxypropenyl side chains generally decrease glucocorticoid receptor antagonist activity in comparison to 17-propinyl side chain containing compounds.

Additional glucocorticoid receptor antagonists known in the art and suitable for practice of the invention include 21-hydroxy-6,19-oxidoprogesterone (see, Vicent, *Mol. Pharm.* 52:749-753, 1997); ORG 31710, (6β,11β,17β)-11-(4-(dimethyl-amino)phenyl)-6-methyl-4',5'-dihydro[estra-4,9-diene-17,2'(3H')-furan]-3-one, (see, Mizutani, *J Steroid Biochem Mol Biol* 42(7):695-704, 1992); ORG 34517, (11β,17β)-11-(1,3-benzodioxol-5-yl)-17-hydroxy-17-(1-propynl)-e-stra-4,9-dien-3-one, as disclosed in Hoyberg et al., *Int'l J. of Neuropsychopharmacology*, 5:Supp. 1, S148 (2002); ORG 33628, [(11β,17α)-11-(4-acetylphenyl)-17,23-epoxy-19,24-dinorchola-4,-9,20-trien-3-one]; ORG 31806, [(7β,11β,17β)-11-(4-(dimethylamino)phenyl)-7-Me-4',5'-dihydrospiro(oestra-4,9-diene-17,2'(3'H)-furan)-3-one]-; ORG 34116, (11β, 17α)-11,21-Bis[4-(dimethylamino)phenyl]-17-hydroxy-19-norpregna-4,9,dien-20-yn-3-one; ORG 34850, (11β,17α)-11-[4-(dimethylamino)phenyl]-17-hydroxy-21-[4-(methylsulfonyl)phenyl-19-norpregna-4,9-dien-20-yn-3-one, and related compounds disclosed in U.S. Pat. No. 5,741,787; RU43044, (17β-hydroxy-11β-4-[methyl]-[1-methylethyl]aminophenyl/-17α-[prop-1-ynyl] estra-4-9-diene-3-one) "RU40555", see Kim, *J Steroid Biochem Mol Biol.* 67(3):213-22, 1998), RU28362, and ZK98299.

B. Non-Steroidal Glucocorticoid Receptor Antagonists

Non-steroidal glucocorticoid receptor antagonists are also used in the methods of the invention to treat patients with a muscular dystrophy. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, *Int. J. Pept. Protein Res.* 43:297-304, 1994; de Bont, *Bioorganic & Medicinal Chem.* 4:667-672, 1996). The creation and simultaneous screening of large libraries of synthetic molecules can be carried out using well-known techniques in combinatorial chemistry, for example, see van Breemen, *Anal Chem* 69:2159-2164, 1997; and Lam, *Anticancer Drug Des* 12:145-167, 1997. Design of peptidomimetics specific for glucocorticoid receptor can be designed using computer programs in conjunction with combinatorial chemistry (combinatorial library) screening approaches (Murray, *J. of Computer-Aided Molec. Design* 9:381-395, 1995; Bohm, *J. of Computer-Aided Molec. Design* 10:265-272, 1996). Such "rational drug design" can help develop peptide isomerics and conformers including cycloisomers, retro-inverso isomers, retro isomers and the like (as discussed in Chorev, *TibTech* 13:438-445, 1995).

Examples of non-steroidal glucocorticoid receptor antagonists include but are not limited to cis-1-acetyl-4-(4-((2-(2,4-dichlorophenyl)-2-(1H-imidazol-1-ylmethyl)-1,3-dioxolan-4-yl)methoxy)phenyl)piperazine; 1-(o-Chloro-alpha,alpha-diphenylbenzyl)imidazole; N (triphenylmethyl) imidazole; N-([2-fluoro-9-phenyl]fluorenyl)imidazole; N-([2-pyridyl]diphenylmethyl)imidazole; N (2 [4,4',4"-trichlorotrityl]oxyethyl)morpholine; 1-(2[4,4',4"-trichlorotrityl]oxyethyl)-4(2 hydroxyethyl)piperazine dimaleate; N-([4,4',4]-trichlorotrityl)imidazole; 9-(3-mercapto-1,2,4 triazolyl)-9-phenyl-2,7-difluorofluorenone; 1-(2-chlorotrityl)-3,5-dimethylpyrazole; 4 (morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-2-methylimidazole; 1 (2 chlorotrityl)-1,2,4-triazole; 1,S-bis(4,4',4"-trichlorotrityl)-1,2,4-triazole-3-thiol; and N ((2,6 dichloro-3 methylphenyl)diphenyl)methylimidazole (see U.S. Pat. No. 6,051,573); the glucocorticoid receptor antagonist compounds disclosed in U.S. Pat. Nos. 5,696,127 and 6,570,020; the glucocorticoid receptor antagonist compounds disclosed in U.S. Pat. Pub. No. 20020077356, the glucocorticoid receptor antagonists disclosed in Bradley et al., *J. Med. Chem.* 45, 2417-2424 (2002), e.g., 4α(S)-Benzyl-2(R)-chloroethynyl-1,2,3,4,4α, 9,10,10α(R)-octahydro-phenanthrene-2,7-diol "CP 394531" and 4α(S)-Benzyl-2(R)-prop-1-ynyl-1,2,3,4,4α,9,10,10α (R)-octahydro-phenanthrene-2,7-diol "CP 409069" and related compounds disclosed in WO 00/66522; the compounds disclosed in WO 96/19458, which describes non-steroidal compounds which are high-affinity, highly selective antagonists for steroid receptors, such as 6-substituted-1,2-dihydro-N-protected-quinolines; benzopyranol[3,4-f] quinolines described as glucocorticoid receptor modulators disclosed in WO 99/41256 and WO 01/16128; aminobenzene derivatives disclosed as glucocorticoid receptor modulators disclosed in WO 02/064550; and some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., *Endocrinol.* 141:2294-2300 (2000); 4β(S)-benzyl-7(S)-hydroxy-7-(1-propynyl)-4β,5,6,7,8,8α(R),9,10-octahydrophenanthrene-2-carboxylic acid (pyridine-4-ylmethyl)amide "CP-472555", 4β(S)-benzyl-7(S)-hydroxy-7-(3,3,3-trifluoropropyl)-4β,5,6,7,8,8α(R),9,10-octahydrophenanthrene-2-carboxylic acid, (2-methylpyridin-3-ylmethyl)amide and related compounds disclosed in WO 0066522 and in US20040176595; octahydrophenanthrenyl carbamates disclosed in EP 1201649; oxadiazolylalkoxyoctahydrophenanthrenes disclosed in EP 1201660; octahydrophenanthrene hydrazines as disclosed in WO 2005/047254; modulators of the glucocorticoid receptor as disclosed in WO 04/005299; tricyclic compounds disclosed in WO 05/011336 and WO 05/011337; Wieland-Miescher ketone derivatives disclosed in WO 03/011755; cyclopent[f]indazole and benz[f]indazole derivatives disclosed in WO 04/075840; spirocyclic compounds disclosed in WO 04/093805; octahydro-2-H-naphtho[1,2,-f]indole-4-carboxamide derivatives disclosed in WO 2004/026248; cholic acid derivatives disclosed in WO 04/000869; dibenzopyran derivatives disclosed in WO 01/16128; 6H-dibenzo[b,d] pyran derivatives disclosed in US20020049322 and US20030220332; substituted aminobenzene derivatives disclosed in WO 02/064550; triphenylmethane derivatives disclosed in U.S. Pat. No. 6,166,013; the compound (3,5-dibromo-4-[5-isopropyl-4-methoxy-2-(3-methylbenzoyl-phenoxy]phenyl)acetic acid "KB285" disclosed in WO 99/63976 and related compounds disclosed in WO 01/047859, WO 02/43648, and WO 02/44120; azadecalin derivatives disclosed in WO 05/070893 and U.S. patent application Ser. No. 10/596,998 (published as US 2007/0203179); fused ring azadecalin compounds disclosed in WO 05/087769 and U.S. patent application Ser. No. 10/591,884 (published as US 2007/0281928); modified pyrimidine compounds disclosed in WO 06/014394 and U.S. patent application Ser. No. 11/174,096 (published as US 2006/0025405).

C. Identifying Specific Glucocorticoid Receptor Antagonists

Because any specific glucocorticoid receptor antagonists can be used to treat muscular dystrophies according to the methods of the invention, in addition to the compounds and compositions described above, additional useful glucocorticoid receptor antagonists can be determined by the skilled artisan. A variety of such routine, well-known methods can be used and are described in the scientific and patent literature. They include in vitro and in vivo assays for the identification of additional glucocorticoid receptor antagonists. A few illustrative examples are described below.

One assay that can be used to identify a glucocorticoid receptor antagonist of the invention measures the effect of a putative glucocorticoid receptor antagonist on tyrosine amino-transferase activity in accordance with the method of Granner, *Meth. Enzymol.* 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxy-benzaldehyde in an alkaline solution and quantitated by absorbance at 331 nm. The putative glucocorticoid receptor antagonist is co-administered with cortisol to whole liver, in vivo or ex vivo, or hepatoma cells or cell extracts. A compound is identified as a glucocorticoid receptor antagonist when its administration decreases the amount of induced TAT activity, as compared to control (i.e., only cortisol or a glucocorticoid receptor agonist added) (see also Shirwany, *Biochem. Biophys. Acta* 886:162-168, 1986).

Further illustrative of the many assays that can be used to identify compositions utilized in the methods of the invention, in addition to the TAT assay, are assays based on glucocorticoid activities in vivo. For example, assays that assess the ability of a putative glucocorticoid receptor antagonist to inhibit uptake of $^3$H-thymidine into DNA in cells stimulated by glucocorticoids can be used. To further identify putative glucocorticoid receptor antagonists, kinetic assays able to discriminate between glucocorticoid receptor agonists and antagonists by means of receptor-binding kinetics can also be used (as described in Jones, *Biochem J.* 204:721-729, 1982).

For additional compounds that can be utilized in the methods of the invention and methods of identifying and making such compounds, see U.S. Pat. No. 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds that are high-affinity, highly selective modulators (antagonists) for steroid receptors, such as 6-substituted-1,2-dihydro N-1 protected quinolines.

The specificity of the antagonist for the glucocorticoid receptor relative to the mineralocorticoid receptor can be measured using a variety of assays known to those of skill in the art. For example, specific antagonists can be identified by measuring the ability of the antagonist to bind to the glucocorticoid receptor compared to the mineralocorticoid receptor (see, e.g., U.S. Pat. Nos. 5,606,021; 5,696,127; 5,215,916; 5,071,773). Such an analysis can be performed using either direct binding assay or by assessing competitive binding to the purified glucocorticoid receptor or mineralocorticoid receptor in the presence of a known antagonist. In an exemplary assay, cells that are stably expressing the glucocorticoid receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the glucocorticoid receptor relative to the mineralocorticoid receptor are then selected for use in the methods of the invention.

A glucocorticoid receptor-specific antagonist may also be defined as a compound that has the ability to inhibit glucocorticoid receptor-mediated activities, but not mineralocorticoid receptor-mediated activities. One method of identifying such a glucocorticoid receptor-specific antagonist is to assess the ability of an antagonist to prevent activation of reporter constructs using transfection assays (see, e.g., Bocquel et al., *J. Steroid Biochem Molec. Biol.* 45:205-215, 1993; U.S. Pat. Nos. 5,606,021 and 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the glucocorticoid receptor and mineralocorticoid receptor (see, e.g., U.S. Pat. No. 5,696,127). Efficacy is then reported as the percent maximal response observed for each compound relative to a reference antagonist compound. A glucocorticoid receptor-specific antagonist is considered to exhibit at least a 100-fold, often 1000-fold or greater, activity towards the glucocorticoid receptor relative to the mineralocorticoid receptor.

VI. Use of Glucocorticoid Receptor Antagonists to Treat Muscular Dystrophies

Glucocorticoid receptor antagonists, such as mifepristone, are formulated as pharmaceuticals to be used in the methods of the invention to treat a muscular dystrophy. Any composition or compound that can block a biological response associated with the binding of cortisol or a cortisol analogue to a glucocorticoid receptor can be used as a pharmaceutical in the invention. Routine means to determine glucocorticoid receptor antagonist drug regimens and formulations to practice the methods of the invention are well described in the patent and scientific literature, and some illustrative examples are set forth below.

A. Pharmaceutical Compositions Containing Glucocorticoid Receptor Antagonists

The glucocorticoid receptor antagonists used in the methods of the invention can be administered by any means known in the art, e.g., parenterally, topically, orally, or by local administration, such as by aerosol or transdermally. The methods of the invention provide for prophylactic and/or therapeutic treatments. The glucocorticoid receptor antagonists as pharmaceutical formulations can be administered in a variety of unit dosage forms depending upon the particular type of symptoms and their severity, the general medical condition of each patient, the preferred method of administration and the like. Details on techniques for formulation and administration are well described in the scientific and patent literature, see, e.g., the latest edition of *Remington's Pharmaceutical Sciences*, Mack Publishing Co, Easton Pa. Therapeutically effective amounts of glucocorticoid receptor antagonist suitable for practice of the method of the invention may range from about 0.5 to about 25 milligrams per kilogram (mg/kg). A person of ordinary skill in the art will be able without undue experimentation, having regard to that skill and this disclosure, to determine a therapeutically effective amount of a particular glucocorticoid receptor antagonist for practice of this invention.

In general, glucocorticoid receptor antagonists may be administered as pharmaceutical compositions by any method known in the art for administering therapeutic drugs. Compositions may take the form of tablets, pills, capsules, semisolids, powders, sustained release formulations, solutions, suspensions, elixirs, aerosols, or any other appropriate compositions; and comprise at least one compound of this invention (a glucocorticoid receptor antagonist) in combination with at least one pharmaceutically acceptable excipient. Suitable excipients are well known to persons of ordinary skill in the art, and they, and the methods of formulating the compositions, may be found in such standard references as Alfonso A R: *Remington's Pharmaceutical Sciences,* 17th ed., Mack Publishing Company, Easton Pa., 1985. Suitable liquid carriers, especially for injectable solutions, include water, aqueous saline solution, aqueous dextrose solution, and glycols.

Aqueous suspensions of the invention contain a glucocorticoid receptor antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, fructose, glucose, sucralose, aspartame, saccharin, or other similar sweetener agents. Formulations can be adjusted for osmolarity.

Oil suspensions can be formulated by suspending a glucocorticoid receptor antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Glucocorticoid receptor antagonist pharmaceutical formulations can be prepared according to any method known to the art for the manufacture of pharmaceuticals. Such formulations can contain sweetening agents, flavoring agents, coloring agents and preserving agents. Any glucocorticoid receptor antagonist formulation can be admixtured with nontoxic pharmaceutically acceptable excipients which are suitable for manufacture.

Typically, glucocorticoid receptor antagonists suitable for use in the practice of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 10% w of the glucocorticoid receptor antagonist, preferably 0.00001% w to 1% w, with the remainder being the excipient or excipients. For example, glucocorticoid receptor antagonist mifepristone is given orally in tablet form, with dosages in the range of between about 0.5 and 25 mg/kg, more preferably between about 0.75 mg/kg and 15 mg/kg, most preferably about 10 mg/kg.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of glucocorticoid receptor antagonists with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxypropyl-methyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

The glucocorticoid receptor antagonists of this invention can also be administered in the form of suppositories for rectal administration. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The glucocorticoid receptor antagonists of this invention can also be administered by in intranasal, intraocular, intravaginal, and intrarectal routes, including suppositories, insufflation, powders, and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The glucocorticoid receptor antagonists of the invention can also be delivered by a transdermal route, such as by a topical route, formulated as applicator sticks, solutions, suspensions, emulsions, gels, creams, ointments, pastes, jellies, paints, powders, and aerosols.

The glucocorticoid receptor antagonists of the invention can also be delivered as microspheres for slow release in the body. For example, microspheres can be administered via intradermal injection of microspheres containing a glucocorticoid receptor antagonist (e.g., mifepristone), which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The glucocorticoid receptor antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use In another embodiment, the glucocorticoid receptor antagonist formulations of the invention are useful for parenteral administration, such as intravenous (IV) administration. The formulations for administration will commonly comprise a solution of a glucocorticoid receptor antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or di-glycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of glucocorticoid receptor antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the glucocorticoid receptor antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the glucocorticoid receptor antagonist into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

B. Determining Dosing Regimens for Glucocorticoid Receptor Antagonists

The methods of this invention are useful for treating patients suffering from a muscular dystrophy. The amount of glucocorticoid receptor antagonist adequate to accomplish this is defined as a "therapeutically effective dose." The dosage schedule and amounts effective for this use, i.e., the "dosing regimen," will depend upon a variety of factors, including the type of muscular dystrophy symptoms a patient has, the severity and duration of such symptoms, the patient's physical status, age, and the like. In calculating the dosage regimen for a patient, the mode of administration also is taken into consideration.

The dosage regimen also takes into consideration pharmacokinetics parameters well known in the art, i.e., the glucocorticoid receptor antagonists' rate of absorption, bioavailability, metabolism, clearance, and the like (see, e.g., Hidalgo-Aragones, *J. Steroid Biochem. Mol. Biol.* 58:611-617, 1996; Groning, *Pharmazie* 51:337-341, 1996; Fotherby, *Contraception* 54:59-69, 1996; Johnson, *J. Pharm. Sci.* 84:1144-1146, 1995; Rohatagi, *Pharmazie* 50:610-613, 1995; Brophy, *Eur. J. Clin. Pharmacol.* 24:103-108, 1983; the latest Remington's, supra). For example, in one study, less than 0.5% of the daily dose of mifepristone was excreted in the urine; the drug bound extensively to circulating albumin (see Kawai, supra, 1989). The state of the art allows the clinician to determine the dosage regimen for each individual patient, glucocorticoid receptor antagonist and disease or condition treated. As an illustrative example, the guidelines provided below for mifepristone can be used as guidance to determine the dosage regiment, i.e., dose schedule and dosage levels, of any glucocorticoid receptor antagonist administered when practicing the methods of the invention.

Single or multiple administrations of glucocorticoid receptor antagonist formulations can be administered depending on the dosage and frequency as required and tolerated by the patient. The formulations should provide a sufficient quantity of active agent, i.e., mifepristone, to effectively ameliorate the symptoms of muscular dystrophy. For example, a typical preferred pharmaceutical formulation for oral administration of mifepristone would be about 5 to 15 mg/kg of body weight per patient per day, more preferably between about 8 to about 12 mg/kg of body weight per patient per day, most preferably 10 mg/kg of body weight per patient per day, although dosages of between about 0.5 to about 25 mg/kg of body weight per day may be used in the practice of the invention. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable glucocorticoid receptor antagonist formulations will be known or apparent to those skilled in the art and are described in more detail in such publications as Remington's, supra. See also Nieman, In "Receptor Mediated Antisteroid Action," Agarwal et al., eds., De Gruyter, New York, 1987.

After a pharmaceutical comprising a glucocorticoid receptor antagonist of the invention has been formulated in a acceptable carrier, it can be placed in an appropriate container and labeled for treatment of an indicated condition. For administration of glucocorticoid receptor antagonists, such labeling would include, e.g., instructions concerning the amount, frequency and method of administration. In one embodiment, the invention provides for a kit for treating a muscular dystrophy condition in a human. The kit includes at least one glucocorticoid receptor antagonist and instructional material teaching the indications, dosage and schedule of administration of the glucocorticoid receptor antagonist.

EXAMPLES

The following examples are provided by way of illustration only and not by way of limitation. Those of skill in the art will readily recognize a variety of non-critical parameters that could be changed or modified to yield essentially the same or similar results.

Example 1

Patient Selection and Testing

Individuals who have been diagnosed with a muscular dystrophy, such as type 1 myotonic dystrophy, are selected to participate the human studies described below. The patient typically has normal levels of cortisol for his or her age, although some with elevated serum cortisol level may be included in the studies in separate groups.

The glucocorticoid receptor antagonist, mifepristone, is used in the studies. It is typically in the range of 50-500 mg for daily administration, for example, in 50 mg, 100 mg, 200 mg, 300 mg daily doses. Individuals will be given their daily dose of mifepristone for a desired time period, e.g., six months, and evaluated as described below. Dosages will be adjusted if necessary and further evaluations will be performed periodically throughout treatment.

Mifepristone tablets are available from commercial sources such as Shanghai HuaLian Pharmaceuticals Co., Ltd., Shanghai, China.

To measure the patients' cortisol levels, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15-28° C.) by gentle swirling or inversion. Sixteen tubes in duplicate at 25 microliters of serum per tube are prepared. Cortisol concentrations are calculated from the prepared calibration tubes. Net counts equal the average CPM minus the average non-specific CPM. Cortisol concentrations for the unknowns are estimated by interpolation from the calibration curve (Dudley et al., *Clin. Chem.* 31: 1264-1271, 1985).

Example 2

Duchene Muscular Dystrophy (DMD) Mouse Studies

Mifepristone is tested in the mdx mouse model of Duchene muscular dystrophy (Grounds et al., 2008, *Neurobiol Dis* 31:1-19) for its ability to improve muscle strength as determined by examining muscle contractility in the dystrophic mice over time and in conjunction with eccentric injury. The mdx mice are C57BL/10ScSn-Dmd$^{mdx}$/J mice with a loss-of-function mutation in the dystrophin gene. They are given mifepristone (1-100 mg per kg body weight, often in the range of 5-50 mg per kg body weight, for example, 5, 10, 20, 30, 40, or 50 mg per kg body weight) or placebo in their food beginning at 4 weeks of age, with each of the test group (mifepristone) and control group (placebo) having about 10-25 animals. After eight weeks of treatment, the effect of mifepristone will be examined be testing the specific force of the extensor digitorum longus muscle, as well as other parameters of contractility. The mdx mice will also be examined for mifepristone's effect on the histological appearance of muscle due to increased or decreased the number of centrally nucleated fibers. Force loss during eccentric contractions and recovery of force following injury will also be examined. Description of experimental procedures can be found in, e.g., Baltgalvis et al., *Muscle Nerve.* 2009 September; 40(3):443-54.

Example 3

DMD Human Studies

Ambulant patients with DMD aged 5 to 8 years are included in a clinical trial of mifepristone. Control group of patients will receive placebo, whereas test groups will receive mifepristone at varying dosages. Patients may be further places in separate groups depending on whether their serum cortisol level is elevated. Each group typically include 5-10 patients. Patients are excluded if they had used steroids within 2 months before the start of the trial. The study receives approval from the local ethics committee and all parents provide written informed consent. In all cases, primary care physicians agree with the patients' participation. The study is a randomized, double-blind, placebo-controlled, crossover design were all patients receive mifepristone or placebo for 6 months After a subsequent washout period of 2 months, patients receive the other regimen for an additional 6 months. during the first 10 days of each month. During the remaining 20 days, no mifepristone or placebo is administered.

The primary outcome measure is a change in muscle function assessed by timed functional testing (running 9 m with bare feet as fast as possible, climbing 4 standard-sized stairs, and rising from a supine position to a standing position on the floor). The secondary outcome measures are changes in quantified muscle force, weight, blood pressure, functional grade, and quality of life (QoL). Changes in muscle force are measured by handheld dynamometry. To determine patterns of muscle weakness, individual muscles are grouped together to calculate changes in clinically relevant summed scores. Total muscle force (all muscle scores added) is distinguished from proximal muscle force (shoulder abductors, elbow flexors and extensors, hip flexors and abductors, knee flexors and extensors), distal muscle force (wrist extensors and 3-point grip), arm muscle force (all arm muscle groups), and leg muscle force (all leg muscle groups).

The functional grade of both upper and lower extremities is measured using the grading system by Brooke et al. (*Muscle Nerve.* 1981; 4:186-197). All measurements are performed each month on days 1, 10, and 30. The quality of life assessment is measured at the start and end of both 6-month trial periods with the DUX-25 by Connolly and Johnson (*Pharmacoeconomics.* 1999; 16:605-625), a QoL questionnaire that covers 4 domains: physical, emotional, social, and home functioning.

Linear regression analysis is used to show changes of the primary and secondary outcome measures in time. For all timed functional tests, muscle force sum scores, weight, and (systolic) blood pressure, the regression coefficient is calculated for both periods. Data are analyzed according to the sequence in which the medication was given. period. Description of experimental procedures can be found in, e.g., Beenakker et al., *Arch Neurol.* 2005; 62:128-132.

Example 4

Myotonic Dystrophy Type 1 (DM1) Mouse Studies

A tamoxifen-inducible heart-specific DM1 mouse model (Wang et al., *J. Clin. Invest.* 117:2802-2811, 2007) is used to test the efficacy and safety of mifepristone to reduce or prevent DM1 related cardiac muscle damage. In this model, EpA960 RNA is induced in the bitransgenic EpA960/MCM mice (F1 progeny) by 5 consecutive daily intraperitoneal injections of tamoxifen (20 mg/kg/d) leading to high mortality, conduction abnormalities, and systolic and diastolic dysfunction. Mifepristone is tested by administering intraperitoneally in saline solution beginning 2 hours after the first tamoxifen injection. Control or mock-treated mice are injected with saline solution alone. Each of the control and test groups typically includes 10-20 mice. The animals are given mifepristone in the range of 1-100 mg per kg body weight, often in the range of 5-50 mg per kg body weight, for example, 5, 10, 20, 30, 40, or 50 mg per kg body weight.

Typically, eighty percent of the mock-treated mice died within 3 weeks of RNA induction due to arrhythmias and/or contractile dysfunction. Administration of mifepristone will reduce the mortality of bitransgenic mice by at least 10%. Description of experimental procedures can be found in, e.g., Wang et al., *J Clin Invest.* 2009; 119(12):3797-806.

Example 5

DM1 Human Studies

A prospective, multicenter, randomized, double-blind, placebo-controlled trial is conducted to investigate the efficacy and safety of the glucocorticoid receptor antagonist mifepristone in myotonic dystrophy type 1 patients. Each of the control and test groups typically includes 5-10 patients. Ambulatory adults with myotonic dystrophy type 1 are randomized to receive daily for 12 weeks, mifepristone (e.g., at 100 mg/day) or placebo, by oral administration. Primary endpoint is the relative change in the manual muscle testing (MMT) score from baseline to week 12. Secondary outcome measures included changes from baseline to week 12 in quantitative muscle testing and timed functional testing, respiratory and cardiac function, and QoL. Description of experimental procedures can be found in, e.g., Penisson-Besnier et al., *Neurology* 2008 Aug. 5; 71(6):407-12.

All patents, patent applications, and other publications cited in this application are incorporated by reference in the entirety for all purposes.

What is claimed is:

1. A method for treating a patient suffering from a muscular dystrophy selected from Duchenne Muscular Dystrophy, myotonic dystrophy 1 and myotonic dystrophy 2, comprising:
   measuring the cortisol level of said patient; then
   administering to the patient a first daily dose of between about 50 milligrams (mg) and about 500 mg of a glucocorticoid receptor antagonist, which inhibits cortisol binding to the glucocorticoid receptor, and binds to the glucocorticoid receptor with an affinity that is at least 100-fold higher than its binding affinity to the mineralocorticoid receptor, wherein said first daily dose is administered on a first day;
   subsequently administering further daily doses of said glucocorticoid receptor antagonist to the patient for at least about 12 weeks to ameliorate the symptoms of the muscular dystrophy; and
   measuring the cortisol level of the patient about two weeks after said first day, wherein the patient is not otherwise in need of treatment with a glucocorticoid receptor antagonist, and wherein said glucocorticoid receptor antagonist.

2. The method of claim 1, wherein the patient suffers from Duchenne Muscular Dystrophy.

3. The method of claim 1, wherein the patient suffers from myotonic dystrophy 1.

4. The method of claim 1, wherein the patient suffers from myotonic dystrophy 2.

5. The method of claim 1, wherein the glucocorticoid receptor antagonist comprises a steroidal skeleton with at least one phenyl-containing moiety in the 11-β position of the steroidal skeleton.

6. The method of claim 5, wherein the phenyl-containing moiety in the 11-β position of the steroidal skeleton is a dimethylaminophenyl moiety.

7. The method of claim 6, wherein the glucocorticoid receptor antagonist is mifepristone.

8. The method of claim 6, wherein the glucocorticoid receptor antagonist is selected from the group consisting of 11β-(4-dimethylaminoethoxyphenyl)-17α-propynyl-17β- hydroxy-4,9 estradien-3-one and 17β-hydroxyl 7α-19-(4-methylphenyl)androsta-4,9(11)-dien-3-one.

9. The method of claim 1, wherein the glucocorticoid receptor antagonist is selected from the group consisting 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol.

10. The method of claim 1, wherein the glucocorticoid receptor antagonist is (11β,17β)-11-(1,3-benzodioxol-5-yl)-17-hydroxy-17-(1-propynyl)estra-4,9-dien-3-one.

11. The method of claim 1, wherein the glucocorticoid receptor antagonist is orally administered.

12. The method of claim 1, wherein the glucocorticoid receptor antagonist is administered by transdermal application, by a nebulized suspension, or by an aerosol spray.

* * * * *

UNITED STATES PATENT AND TRADEMARK OFFICE
CERTIFICATE OF CORRECTION

PATENT NO. : 11,103,514 B2
APPLICATION NO. : 13/116239
DATED : August 31, 2021
INVENTOR(S) : Joseph Belanoff Page 1 of 1

It is certified that error appears in the above-identified patent and that said Letters Patent is hereby corrected as shown below:

In the Claims

In Column 20, Lines 48 and 49, Claim 1, delete ", and wherein said glucocorticoid receptor antagonist"

In Column 21, Line 1, Claim 8, delete "hydroxyl-4,9 estradien-3-one and 17β-hydroxyl 7α-19-(4-" and replace with --hydroxyl-4,9-estradien-3-one and 17β-hydroxy-17α-19-(4- --

In Column 21, Line 4, Claim 9, delete "consisting" and replace with --consisting of--

Signed and Sealed this
Fifth Day of October, 2021

Drew Hirshfeld
*Performing the Functions and Duties of the
Under Secretary of Commerce for Intellectual Property and
Director of the United States Patent and Trademark Office*